United States Patent [19]

Ryang

[11] Patent Number: 4,511,701

[45] Date of Patent: Apr. 16, 1985

[54] HEAT CURABLE EPOXY RESIN COMPOSITIONS AND EPOXY RESIN CURING AGENTS

[75] Inventor: Hong-Son Ryang, Camarillo, Calif.

[73] Assignee: General Electric Company, Schenectady, N.Y.

[21] Appl. No.: 584,068

[22] Filed: Feb. 27, 1984

[51] Int. Cl.$^3$ ............................................... C08G 59/14
[52] U.S. Cl. ............................... 525/533; 525/487; 525/488; 528/25; 528/26; 528/27; 528/28; 549/234
[58] Field of Search ................ 525/533, 487, 488; 528/25, 27, 26, 28; 549/234

[56] References Cited

U.S. PATENT DOCUMENTS

| | | |
|---|---|---|
| 2,935,488 | 5/1960 | Phillips et al. |
| 3,235,620 | 2/1966 | Phillips et al. |
| 3,369,055 | 2/1968 | Salyer et al. |
| 3,379,653 | 4/1968 | Ernst et al. |
| 3,398,211 | 8/1968 | Ramos |
| 3,403,199 | 9/1968 | Ramos |
| 3,563,850 | 2/1971 | Stackhouse et al. |
| 3,567,797 | 3/1971 | Mango et al. |
| 3,677,995 | 7/1972 | Earing |
| 3,775,442 | 11/1973 | Hughes |
| 4,058,401 | 11/1977 | Crivello ........................ 204/159.22 |
| 4,216,288 | 8/1980 | Crivello ........................ 204/159.23 |
| 4,381,396 | 4/1983 | Ryang ........................... 549/234 |

OTHER PUBLICATIONS

Chemical Abstracts, 72, 32777m, (1970), USSR 244,616, (1969), Moshinskii.

Encyclopedia of Polymer Science and Technology, vol. 6, 1967, Interscience Publishers, New York, pp. 209–271.

*Primary Examiner*—Melvyn I. Marquis
*Attorney, Agent, or Firm*—William A. Teoli; James C. Davis, Jr.; James Magee, Jr.

[57] ABSTRACT

Curable epoxy resin compositions are provided resulting from the use of a silylnorbornane functional anhydride or imidoamine. The cured products show improved thermal and physical properties as compared to conventional curing agents.

2 Claims, No Drawings

HEAT CURABLE EPOXY RESIN COMPOSITIONS AND EPOXY RESIN CURING AGENTS

BACKGROUND OF THE INVENTION

Prior to the present invention, various procedures were used to cure epoxy resins. For example, Crivello, U.S. Pat. No. 4,058,401 shows that epoxy resins can be cured by use of a photoinitiator, such as a triarylsulfonium salt in combination with exposure to actinic irradiation, such as ultraviolet light. Methods for effecting the cure of epoxy resins by heat are shown by Crivello, U.S. Pat. No. 4,216,288, directed to heat curable cationically polymerizable organic materials using an aromatic onium salt initiator, such as an aromatic sulfonium salt and a reducing agent, such as thiophenol. Additional procedures for effecting the cure of epoxy resins which do not require the use of arylsulfonium salts and which impart improved toughness to the resulting cured epoxy resin is by the use of organic anhydrides for functionalized organosiloxanes, as shown by Moshinskii et al. U.S.S.R. 244616 (1969) [Chemical Abstracts 72 32777m (1970)]. However, the use of functionalized siloxanes as reported by Moshinskii et al suffer from the fact that the method of preparing the silicone curing agent is uneconomic, or the resulting cured epoxy resin is not stable enough for certain high temperature applications.

The present invention is based on the discovery that heat curable epoxy resin compositions can be made having improved heat distortion temperature at elevated temperatures and improved oxidative stability as well as providing elastomeric organopolysiloxanes having improved toughness by utilizing as a curing agent for the epoxy resin an effective amount of an organopolysiloxane having attached to silicon by carbon-silicon linkages at least one group of the formula,

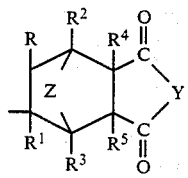
(1)

and thereafter heating the resulting blend at a temperature in the range of between about 50° C. to 300° C., where $R$—$R^5$ are members selected from hydrogen, halogen, $C_{(1-13)}$ monovalent hydrocarbon radicals and substituted $C_{(1-13)}$ monovalent hydrocarbon radicals, Z is selected from —O— and C—$(R)_2$ and Y is a member selected from —O— and

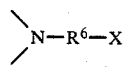

$R^6$ is a divalent $C_{(1-13)}$ hydrocarbon radical or substituted hydrocarbon radical and X is a monovalent amine radical.

STATEMENT OF THE INVENTION

There is provided by the present invention curable epoxy resin compositions comprising:
(A) an epoxy resin and
(B) an effective amount of organopolysiloxane curing agent having attached to silicon by carbon-silicon bonds at least one group of formula (1).

Radicals included within R—$R^5$ of formula (1) are, for example, halogen such as chloro, bromo, etc. In addition, R—$R^5$ radicals also include, aryl radicals and halogenated aryl radicals, for example, phenyl, chlorophenyl, tolyl, xylyl, biphenyl, naphthyl, etc.; alkenyl radicals for example, vinyl, allyl, cyclohexenyl, etc.; $C_{(1-8)}$ alkyl radicals, halogenated alkyl and aminoalkyl radicals, for example, methyl, ethyl, propyl, butyl, octyl, etc. $R^6$ is selected from divalent $C_{(1-8)}$ alkyl radicals, for example, methylene, dimethylene, trimethylene; $C_{(6-13)}$ arylene radicals such as phenylene tolylene, xylylene naphthalene. In instances where R—$R^6$ is more than one radical, these radicals can be all the same or any two or more of the aforementioned radicals.

Curing agents which can be utilized in the practice of the present invention to make the heat curable epoxy resin compositions are, for example, silylnorbornane anhydrides shown in Ryang U.S. Pat. No. 4,381,396, which is incorporated herein by reference. For example, there can be used siloxane norbornane anhydrides such as

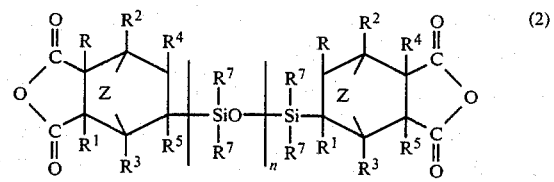
(2)

where R—$R^5$ and Z are as previously defined, n is an integer equal to 1 to 2,000 and $R^7$ is selected from $C_{(1-13)}$ monovalent hydrocarbon radicals and substituted monovalent hydrocarbon radicals such as methyl, phenyl and vinyl, etc.

In addition to the organic anhydrides, there can be used as curing agents in the practice of the present invention imidoamino norbornane functional organosiloxane having attached to silicon by carbon-silicon bonds at least one group of the formula,

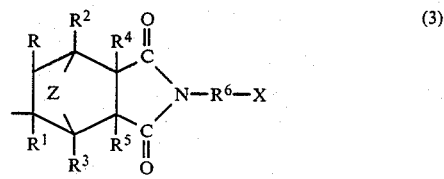
(3)

where R—$R^5$, Z, $R^6$ and X are as previously defined.

Some of the imidoamino norbornane functional organosiloxanes of formula (3) are, for example,

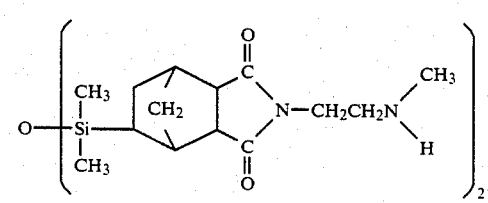

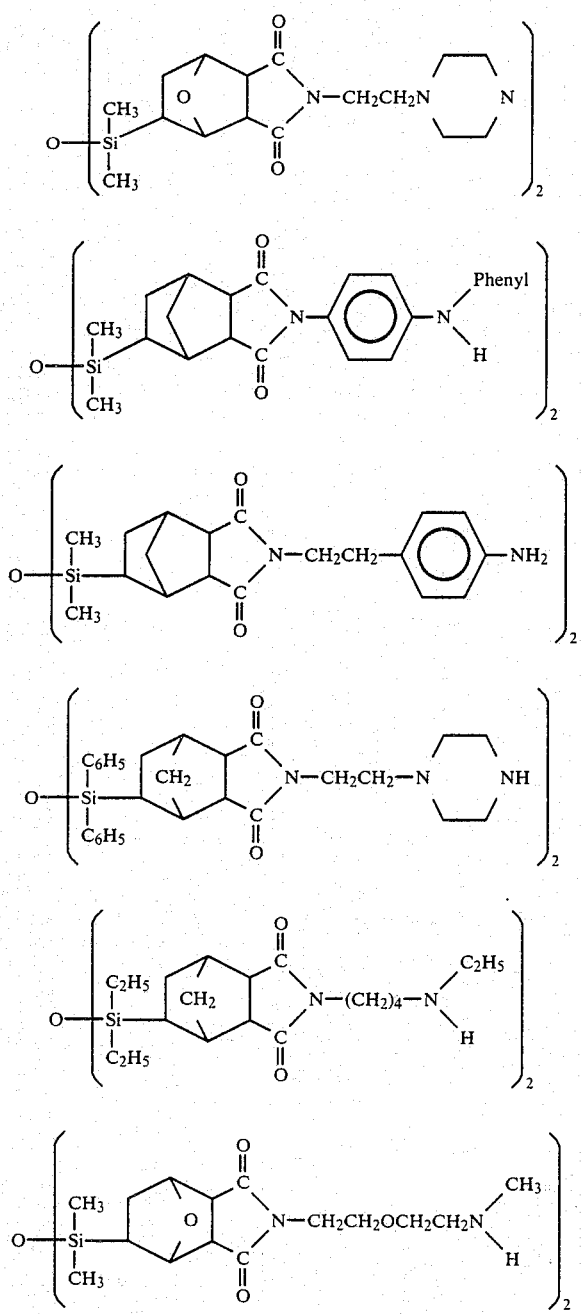

The term "epoxy resin" as utilized in the description of the curable compositions of the present invention, includes any monomeric, dimeric or oligomeric or polymeric epoxy material containing one or a plurality of epoxy functional groups. For example, those resins which result from the reaction of bisphenol-A (4,4'-isopropylidenediphenol) and epichlorohydrin, or by the reaction of low molecular weight phenol-formaldehyde resins (Novolak resins) with epichlorohydrin, or by the reaction of low molecular weight phenol-formaldehyde resins (Novolak resins) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above catalysts are epoxy-siloxane resins, epoxy-polyurethanes and epoxy-polyesters. Such polymers usually have epoxy functional groups at the ends of their chains. Epoxy-siloxane resins and methods for making are more particularly shown by E. P. Pluedemann and G. Fanger, J. Am. Chem. Soc. 81 632-5 (1959). As described in the literature, epoxy resins can also be modified in a number of standard ways such as reactions with amines, carboxylic acids, thiols, phenols, alcohols, etc., as shown in U.S. Pat. Nos. 2,935,488; 3,235,620; 3,369,055; 3,379,653; 3,398,211; 3,403,199; 3,563,850; 3,567,797; 3,677,995; etc. Further examples of epoxy resins which can be used are shown in the Encyclopedia of Polymer Science and Technology, Vol. 6, 1967. Interscience Publishers, New York, pp. 209-271.

In the practice of the present invention, the heat curable epoxy resin compositions can be made by merely blending together the epoxy resin and the curing agent. Depending upon the nature of the curing agent, that is whether it is a norbornane anhydride functional siloxane, norbornane imide organoamine siloxane, or whether the value of n in the organosiloxane block has a value of from 1 to 50, or 1000 or higher, the amount and the manner by which cure of the resulting epoxy resin composition is achieved can vary widely. It has been found, for example, that effective results can be achieved if sufficient curing agent is employed to provide at least from 0.01 to 10 moles of anhydride, or amine, per mole of oxirane oxygen of the epoxy resin.

The imidoamino norbornane functional organosiloxanes having at least one group of formula (3) can be made by effecting reaction at temperatures between 100° to 200° C. of compounds containing at least two amino groups such as

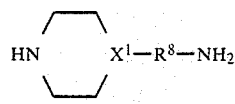

where $X^1$ is selected from N or CH and $R^8$ is a $C_{(1-13)}$ divalent hydrocarbon radical. The reaction can be facilitated by use of an inert organic solvent such as xylene or other hydrocarbon or chlorinated hydrocarbon capable of providing removal of water by azeotropic distillation.

It has been found that cure of the heat curable epoxy resin composition containing norbornane anhydride siloxane can be facilitated by the employment of a small amount of organic amine such as benzyldimethylamine sufficient to provide 1.0 to 10 parts of organic amine per part of heat curable epoxy resin composition. Of course, organic amine catalyst is not necessary when utilizing norbornane substituted siloxane having imidoorganoamine functional groups as shown by formula 3 above.

In instances where the value of n in the organosiloxane block as shown in formula 2 and including formula 3 has a value greater than 6, the resulting cured epoxy resin compositions can be tough elastomers depending upon the weight percent of the organosiloxane in the total cured epoxy resin composition. High strength elastomers can be made, for example, by utilizing 100 parts of the epoxy resin and from 50 to 2000 parts of the norbornane siloxane curing agent where the value of n in the siloxane block can be from 6 to 50.

The heat curable epoxy resin compositions also can contain common additives such as fillers, pigments, solvents, reinforcing fibers, mold release agents, thixotropic agents, corrosion inhibitors, plasticisers, and the like.

In addition to high strength elastomers and sealants, the heat curable epoxy resin compositions of the present invention have shown good adhesion to many substrates such as glass, steel, aluminum and wood and useful as molding and potting compounds, adhesives, coatings and sealants.

In order that those skilled in the art will be better able to practice the invention, the following examples are given by way of illustration and not by way of limitation. All parts are by weight.

EXAMPLE 1

There was added 10 drops of a 5% platinum catalyst prepared in accordance with Karstedt, U.S. Pat. No. 3,775,442, assigned to the same assignee as the present invention, to a mixture while it was being stirred of 69.4 g (0.42 mole) of 5-norbornene-2,3-dicarboxylic acid anhydride, 26.8 g (0.2 mole) 1,1,3,3-tetramethyldisiloxane and 100 ml of dry chlorobenzene. The resulting mixture was heated with stirring to 70°–80° C. for 4 hours and then 100°–110° C. overnight. After cooling, carbon black was added and the solution was stirred for 30 minutes at room temperature. Filtration, removal of the solvent at 100° C. with a vacuum pump and addition of dry diethylether resulted in the precipitation of a while crystalline solid. Based on method of preparation, the product was 5,5′-(1,1,3,3-tetramethyl-1,3-disiloxanediyl)-bis-norbornane-2,3-dicarboxylic anhydride having the formula, The identity of the above dianhydride was further confirmed by NMR, IR, mass spectrometry and elemental analysis.

A blend of the above dianhydride and Epon 828 which is a diglycidyl ether of BPA of the Shell Chemical Company was made. The proportions utilized in the blend were sufficient to provide a ratio of anhydride to epoxy having a value of about 0.84. The blend was heated to 160° C. under substantially anhydrous conditions to produce a clear mixture which was stable for more than 2 weeks at room temperature. There was added to the resulting blend 1 part of benzyldimethylamine, per 100 parts Epon 828 resulting in the production of a transparent cured resin.

The heat distortion temperature and the oxidative stability of the cured epoxy resin was compared to the cured product obtained from the same epoxy resin utilizing commercially available 4-methylhexahydrophthalic anhydride (MHHPA). The following results were obtained, where the above dianhydride is used in the practice of the present invention:

TABLE I

| | | | TGA (°C.) | | | |
|---|---|---|---|---|---|---|
| | | | 1% WT Loss | | 10% WT Loss | |
| Anhydride | A/E | HDT (°C.) | N₂ | Air | N₂ | Air |
| Dianhydride | 0.84 | 189 | 360 | 330 | 415 | 410 |
| MHHPA | 0.84 | 120 | 350 | 330 | 385 | 380 |

The above results show that the norbornane anhydride siloxane curing agent of the present invention provides cured epoxy resins having improved heat distortion temperature.

EXAMPLE 2

In accordance with a procedure similar to Example 2 of Ryang, U.S. Pat. No. 4,381,396, there was prepared a polydimethylsiloxane having an average of about 50 chemically combined dimethylsiloxy units terminated with 5-norbornane-2,3-dicarboxylic anhydride groups. There was added 21.06 grams of the norbornane dianhydride over a 10 minute period to a solution of 1.36 grams of N-(2-Aminoethyl)-piperazine in 50 ml of toluene and 50 ml of xylene under nitrogen. There was obtained a highly viscous solution which was refluxed for 2 hours during which time water was removed azeotropically. After removal of the solvent, the residue was further heated to 150° C. under vacuum to remove volatile materials. Based on method of preparation, there was obtained a polydimethylsiloxane having terminal norbornane imide secondary amine groups having the formula,

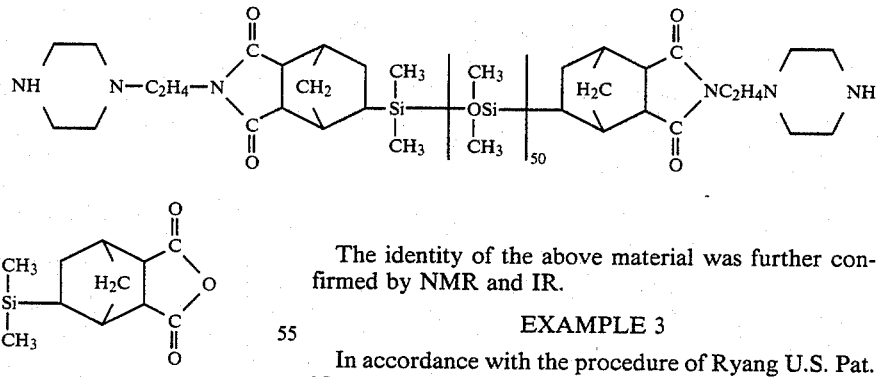

The identity of the above material was further confirmed by NMR and IR.

EXAMPLE 3

In accordance with the procedure of Ryang U.S. Pat. No. 4,381,396, there was prepared a polydimethylsiloxane having an average of about 26 chemically combined dimethylsiloxy units and terminated with 5-norbornane-2,3-dicarboxylic anhydride groups. There was added 23.12 grams of the dianhydride over a 10 minute period under nitrogen to a mixture of 2.40 grams of 4-aminomethylpiperdine, 50 ml of toluene and 50 ml of xylene. The resulting highly viscous mixture was refluxed for 2 hours to effect the azeotropic removal of water of reaction. After removal of solvent, the mixture was further heated to 150° C. to eliminate any unreacted starting amine. Based on method of preparation, there was obtained a polydimethylsiloxane having terminal imide norbornane secondary amine groups having the formula

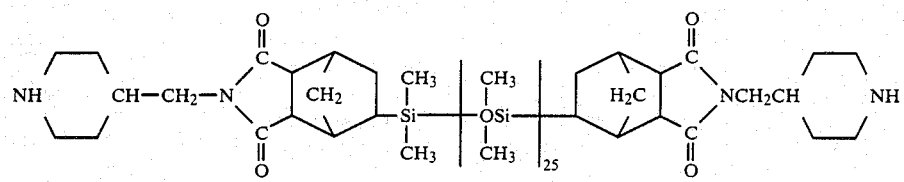

The identity of the above material was further confirmed by NMR.

EXAMPLE 4

A blend was prepared of 3.32 grams of the curing agent of Example 2 and 0.43 grams of the diglycidyl ether of bisphenol-A (Epon 828). Upon mixing the ingredients in a glass dish at room temperature, there was obtained a white, opaque viscous gel. The gel was heated to a 120° C. for 2 hours and 150° C. for 15 hours. There was obtained an elastomer having a tensile strength (psi) of 332 and an elongation (percent) of 490.

The same procedure was repeated, except that in place of the diglycidyl ether of bisphenol-A there was used a novolac epoxy resin (DEN431) of the Dow Chemical Company.

There was obtained cured elastomers showing improved strength compared to polydimethylsiloxane homopolymers. Thermogravimetric analysis (TGA) of the elastomers are shown as follows:

TABLE II

| | TGA (°C.) | | | |
|---|---|---|---|---|
| | 1% WT Loss | | 10% WT Loss | |
| Substrate | $N_2$ | Air | $N_2$ | Air |
| Epon 828 | 330 | 300 | 420 | 405 |
| Novolac Den 431 | 350 | 320 | 430 | 420 |

The above results show that that cured elastomers of the present invention exhibit toughness and oxidative stability. In addition, the cured elastomers also showed good adhesion to glass and aluminum.

EXAMPLE 5

There was mixed 1 g of an aminoimido siloxane curing agent of the formula

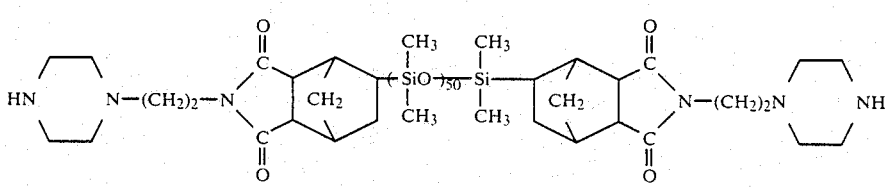

with a mixture of 0.33 g Epon 828 and 0.08 g of bisphenol-A which had been mixed at 100° C. for 10 minutes.

The resulting opaque gel was allowed to stand at room temperature for 3 days. The cured elastomer was transluscent and showed good adhesion to glass.

EXAMPLE 6

There was mixed 1.27 g of an aminoimido siloxane curing agent of the formula

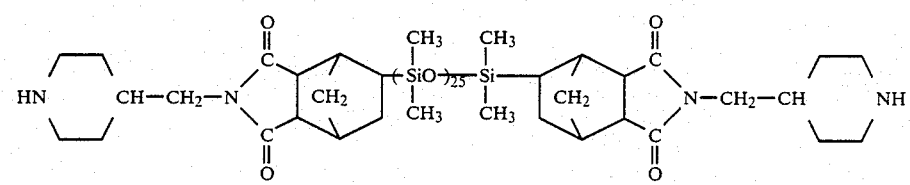

with a Novolac epoxy resin (DEN431) in a glass dish at room temperature. The resulting opaque gel was heated at 120° C. for 2 hours and 150° C. for 4 hours. The cured elastomer was transluscent and showed good adhesion to glass.

Although the above examples are directed to only a few of the very many epoxy resin compositions of the present invention, as well as aminoimidonorbornane siloxane curing agents and methods for making such materials, it should be understood that the present invention is directed to a much broader variety of such compositions and curing agents as shown in the description preceding these examples.

What we claim as new and desire to secure by Letters Patent of the United States is:

1. Curable epoxy resin compositions comprising
   (A) an epoxy resin and
   (B) an effective amount of organopolysiloxane curing agent having attached to silicon by carbon-silicon bonds at least one group of the formula,

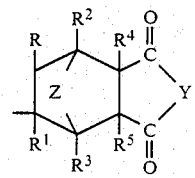

where $R$—$R^5$ are members selected from hydrogen, halogen, $C_{(1-13)}$ monovalent hydrocarbon radicals and substituted $C_{(1-13)}$ monovalent hydrocarbon radicals, Z is selected from —O— and C—(R)$_2$ and Y is a member selected from —O— and
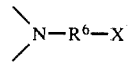
$R^6$ is a divalent $C_{(1-13)}$ hydrocarbon radical or substituted hydrocarbon radical and X is a monovalent amine radical.
2. Tough elastomers resulting from the heat cure of compositions of claim 1.
* * * * *